US00PP27941P3

(12) United States Plant Patent
Ui et al.

(10) Patent No.: US PP27,941 P3
(45) Date of Patent: Apr. 25, 2017

(54) ***PETUNIA-CALIBRACHOA* HYBRID PLANT NAMED 'SAKPXC014'**

(50) Latin Name: ***Petunia-Calibrachoa* intergeneric hybrid**
Varietal Denomination: SAKPXC014

(71) Applicant: Sakata Seed Corporation, Yokohama (JP)

(72) Inventors: Akinobu Ui, Iwata (JP); Shin Ishikawa, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 101 days.

(21) Appl. No.: 14/544,838

(22) Filed: Feb. 24, 2015

(65) Prior Publication Data

US 2016/0249518 P1 Aug. 25, 2016

(51) Int. Cl.
*A01H 5/02* (2006.01)

(52) U.S. Cl.
USPC ..... Plt./356.11

(58) Field of Classification Search
USPC ..... Plt./356.11, 413
See application file for complete search history.

*Primary Examiner* — Keith Robinson
(74) *Attorney, Agent, or Firm* — Barbara Campbell; Bethany R. Roahrig; Cochran Freund & Young, LLC

(57) ABSTRACT

A new *Petunia-Calibrachoa* hybrid plant particularly distinguished by having purple flower color and a spreading plant habit, is disclosed.

1 Drawing Sheet

Genus and species: *Petunia-Calibrachoa* intergeneric hybrid.

Variety denomination: 'SAKPXC014'.

BACKGROUND OF THE NEW PLANT

The present invention comprises a new and distinct variety of *Petunia-Calibrachoa* (Petchoa) referred to by the variety name 'SAKPXC014'. Variety 'SAKPXC014' originated as a plant mutation from the parent plant 'Kakegawa S89' (U.S. Plant Pat. No. 19,130), also commercially known as SUPERCAL 'Neon Rose' in a greenhouse in Kakegawa, Japan in May 2009. The new line was given the experimental name 'K2010-J-122'.

In July 2009, 'K2010-J-122' was first propagated and cultivated in Kakegawa, Japan. In November 2009, 'K2010-J-122' was observed to have its distinct characteristics remain stable. In December 2009, 'K2010-J-122' was propagated again and plants were cultivated. In April 2010, 'K2010-J-122' was confirmed that the distinct characteristics of the plant were fixed and stable. The plant was later named 'SAKPXC014' and was found to reproduce true to type in successive generations of asexual propagation via vegetative cuttings in Salinas, Calif.

SUMMARY

The following are the most outstanding and distinguishing characteristics of this new variety when grown under normal horticultural practices in Salinas, Calif.

1. Purple flower color; and
2. A spreading plant habit.

DESCRIPTION OF THE PHOTOGRAPHS

This new *Petunia-Calibrachoa* plant is illustrated by the accompanying photographs which show the plant's overall plant habit including form, foliage, and flowers. The photographs are of a 6 month old plant grown in Salinas, Calif. under greenhouse conditions in spring 2014. The colors shown are as true as can be reasonably obtained by conventional photographic procedures.

DESCRIPTION OF THE NEW VARIETY

Figure 1:
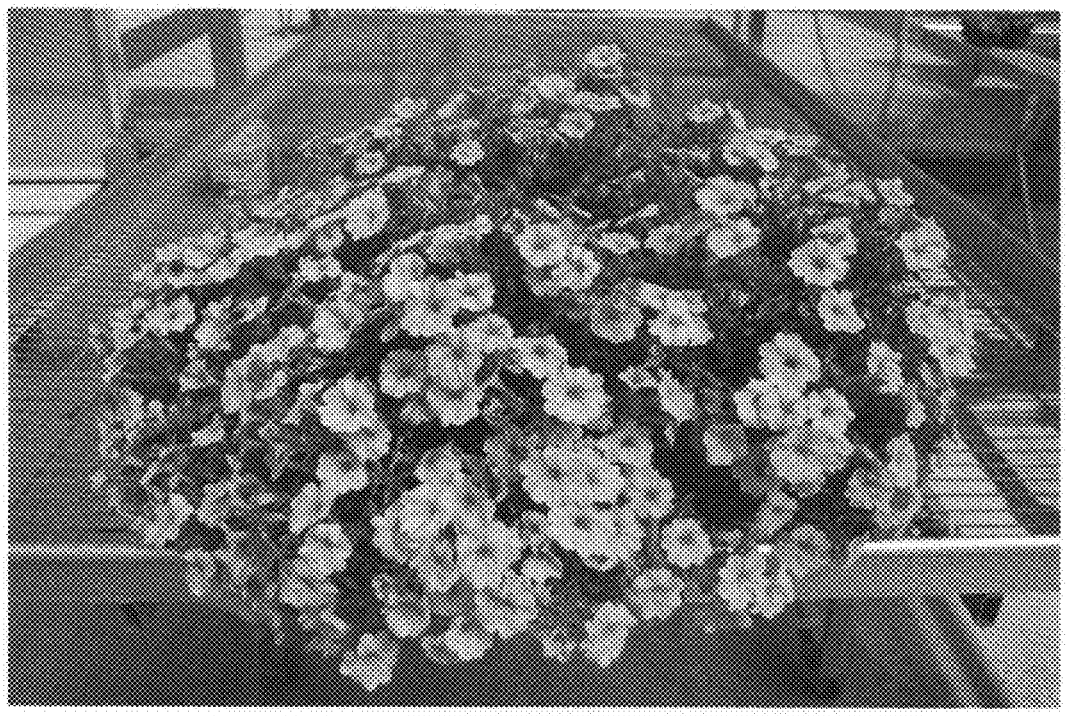
FIG. 1 shows the overall plant habit of the plant grown in a pot.
Figure 2:
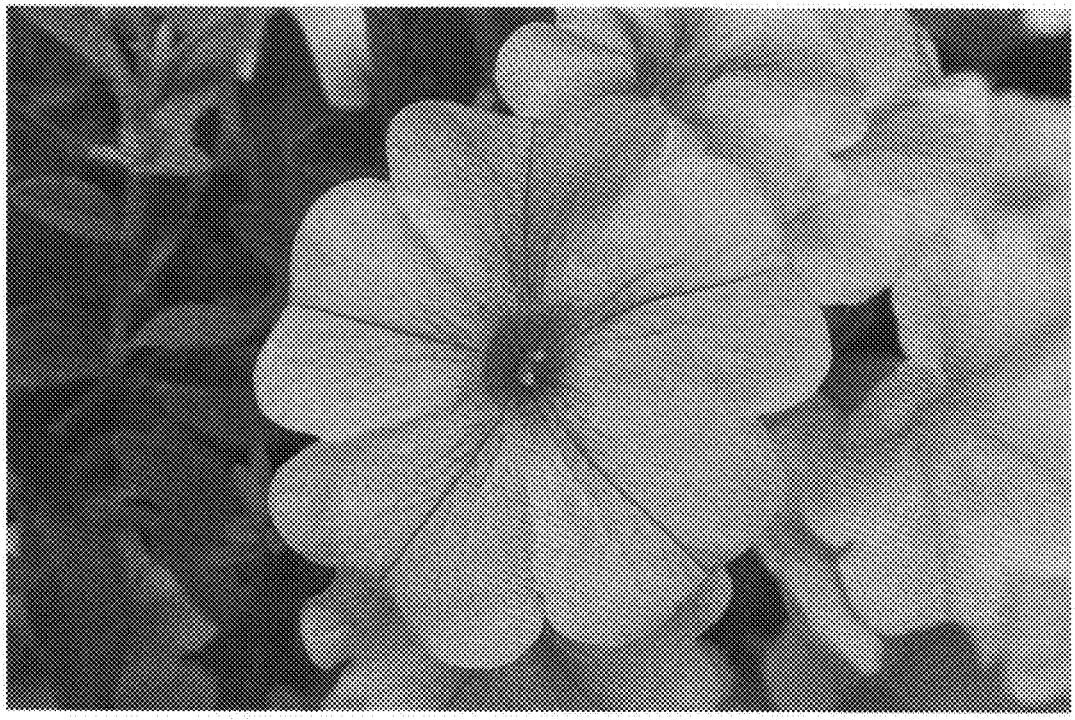
FIG. 2 shows a close-up of the foliage and flower.

The following detailed descriptions set forth the distinctive characteristics of 'SAKPXC014'. The data which define these characteristics were collected from asexual reproductions carried out in Salinas, Calif. Data was collected on six month old plants grown under greenhouse conditions in Salinas, Calif. in spring 2014. Color references are to The R.H.S. Colour Chart of The Royal Horticultural Society of London (R.H.S.), 4$^{th}$ edition, 2001. Anatomic labels are from *The Cambridge Illustrated Glossary of Botanical Terms*, by M. Hickey and C. King, Cambridge University.

Classification:

*Family*.—Solanaceae.
*Botanical*.—*Petunia-Calibrachoa* hybrid.
*Common*.—Petchoa, *petunia-calibrachoa*.
*Designation*.—'SAKPXC014'.

Parentage:

*Mutation parent*.—'Kakegawa S89' (U.S. Plant Pat. No. 19,130).

Growth:

*Time to produce a rooted cutting*.—6 weeks.
*Time to bloom from propagation*.—10 weeks.
*Environmental conditions for plant growth*.—The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution:9 water), a root inducing solution, immediately prior to sticking into the cell trays. Cuttings were stuck into plastic cell trays having 98 cells, and containing a moistened peat moss-based growing medium. For the first week, the cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Plant description:

*Habit.*—Spreading.
*Life cycle.*—Tender perennial.
*Natural flowering season.*—Spring to autumn.
*Height (from soil line to top of foliage).*—24.0 cm.
*Spread.*—90.0 cm.
*Form.*—Decumbant, branching.

Stems:

*General.*—Dull in appearance and circular in cross-section.
*Stem length.*—26.0 cm in length from end to end; 0.5 cm from soil line to first node.
*Diameter.*—0.3 cm.
*Internode length.*—3.0 cm.
*Color.*—RHS 143A (Green) with some anthocyanin, RHS N187A (Greyed-Purple).
*Pubescence.*—Moderate, color is RHS N155A (White).
*Strength.*—Medium.

Leaves:

*Arrangement.*—Alternate.
*Shape.*—Elliptic.
*Apex.*—Obtuse.
*Base.*—Attenuate.
*Margin.*—Entire.
*Venation.*—Pinnate.
*Surface appearance (both surfaces).*—Dull.
*Surface pubescence (both surfaces).*—Very slight; pubescence is RHS N155A (White).
*Length.*—4.0 cm.
*Width.*—1.5 cm.
*Color.*—Upper surface: RHS 137A (Green). Lower surface: RHS 137C (Green).
*Fragrance.*—Absent.
*Petiole.*—Absent.

Flowers:

*Flowering habit.*—Indeterminate.
*Flower type.*—Solitary.
*Flowering requirements.*—Will flower so long as day length is greater than 12 hours and temperature exceeds 13° C.
*Duration of flowers.*—5 days.
*Shape.*—The flowers are funnel shaped with five fissures and a shallow, yet prominent, indentation of the petal tip at the midvein.
*Fragrance.*—Absent.
*Longevity of the flower.*—Approximately 5 days.

Flower buds:

*Surface texture.*—Pubescent.
*Length.*—2.5 cm.
*Diameter.*—0.4 cm.
*Shape.*—Ovate.
*Color.*—RHS 1C (Green-Yellow) with RHS N77A (Purple) veins and RHS N77D (Purple) at the tip.

Peduncle:

*Length.*—2.0 cm.
*Diameter.*—0.1 cm.
*Color.*—RHS 143A (Green).
*Texture.*—Dull, slight pubescence, pubescence color is RHS N155A (White).
*Strength.*—Medium.

Flower description:

*Flower depth.*—0.5 cm.
*Flower diameter.*—4.5 cm.
*Flower tube length.*—2.0 cm.
*Flower tube diameter.*—0.6 cm.

Calyx:

*Arrangement.*—Composed of 5 sepals, fused below the middle.
*Sepals.*—Shape: Elliptic. Apex: Obtuse. Margin: Entire. Length: 2.5 cm. Diameter: 5.0 mm. Color: RHS 137A (Green) on the upper surface and RHS 137C (Green) on the lower surface. Texture (both surfaces): Dull.

Corolla:

*Arrangement.*—Composed of 5 petals, fused.
*Petal.*—Shape: Funnel-shaped with 5 fissures and a shallow, yet slight, indentation of the petal tip at the mid-vein. Apex: Truncate. Margin: Entire. Base: Fused. Pubescence (both surfaces): Glabrous. Length: 3.0 cm. Width: 2.0 cm. Color: Upper surface: RHS N78C (Purple) and RHS 69C (Red-Purple) with RHS N163 (Greyed-Orange) veins. Lower surface: RHS 69C (Red-Purple) with RHS 151C (Yellow-Green) veins.
*Corolla tube color.*—Inner: RHS 12A (Yellow) with RHS N77A (Purple) veins. Outer: RHS 8A (Yellow) with RHS N77A (Purple) and RHS 151C (Yellow-Green) veins.

Reproductive organs:

*Stamen number.*—5, free.
*Stamen length.*—1.0 cm.
*Anther color.*—2A (Yellow).
*Anther length.*—0.2 cm.
*Stamen color.*—RHS 145D (Yellow-Green).
*Filament color.*—RHS 1D (Yellow).
*Filament length.*—0.8 cm.
*Pollen color.*—RHS 2A (Yellow).
*Pollen amount.*—Abundant.
*Ovary.*—Superior.
*Ovary color.*—RHS 144B (Yellow-Green).
*Placenta arrangement.*—Central.
*Pistil number.*—1 per inflorescence.
*Pistil length.*—1.4 cm.
*Stigma color.*—RHS 145A (Yellow-Green).
*Stigma shape.*—Transversely ellipsoidal.
*Style length.*—1.3 cm.
*Style color.*—RHS 145A (Yellow-Green).

Seed production: None observed.

Environmental conditions, disease and insect resistance: Excellent resistance to rain, heat and drought. Will tolerate light frost and recover. Plants are susceptible to

*Botrytis*, various stem and root rots, Tobacco Mosaic Virus and Impatiens Necrotic Spotted Virus. Plants can be infested with aphids, leafminer, whitefly and various *Lepidoptera*.

COMPARISON WITH PARENTAL LINE AND KNOWN VARIETY

'SAKPXC014' is distinguished from its mutation parent mainly as shown in Table 1 below:

TABLE 1

| Characteristic | 'SAKPXC014' | Mutation Parent 'Kakegawa S89' |
|---|---|---|
| Petal color, upper surface | RHS N78C (Purple) and RHS 69C (Red-Purple) with RHS N163 (Greyed-Orange) veins | RHS N66A (Purple) with RHS 64A (Red-Purple) veins |
| Petal color, lower surface | RHS 69C (Red-Purple) with RHS 151C (Yellow-Green) veins | RHS N66C (Red-Purple) with RHS 142A (Green) veins |

'SAKPXC014' can be compared to the *Petunia-Calibrachoa* hybrid plant 'SAKPXC009' (U.S. Plant Pat. No. 23,372) as shown in Table 2:

TABLE 2

| Characteristic | 'SAKPXC014' | 'SAKPXC009' |
|---|---|---|
| Petal color, upper surface | RHS N78C (Purple) and RHS 69C (Red-Purple) with RHS N163 (Greyed-Orange) veins | Closest to RHS N74A (Red-Purple) |
| Petal color, lower surface | RHS 69C (Red-Purple) with RHS 151C (Yellow-Green) veins | Closest to RHS 76D (Purple) with sprays of RHS N74C (Red-Purple) and RHS 59A (Red-Purple) veins |

We claim:

1. A new and distinct cultivar of *Petunia-Calibrachoa* hybrid plant as shown and described herein.

* * * * *